United States Patent
Vanden Hoek et al.

[11] Patent Number: 5,857,961
[45] Date of Patent: Jan. 12, 1999

[54] SURGICAL INSTRUMENT FOR USE WITH A VIEWING SYSTEM

[75] Inventors: John C. Vanden Hoek, Elk River; Thomas A. Poss, St. Louis Park, both of Minn.

[73] Assignee: Clarus Medical Systems, Inc., Minneapolis, Minn.

[21] Appl. No.: 596,073

[22] Filed: Feb. 6, 1996

Related U.S. Application Data

[63] Continuation-in-part of Ser. No. 472,187, Jun. 7, 1995, Pat. No. 5,667,473.

[51] Int. Cl.$^6$ ........................................ A61B 1/005
[52] U.S. Cl. .................... 600/104; 600/156; 600/172; 600/182
[58] Field of Search ........................ 600/101, 104, 600/113, 114, 153, 182, 175, 139, 156, 159; 604/20; 433/29, 31; 606/15, 16, 46, 167, 170, 205, 211, 207

[56] References Cited

U.S. PATENT DOCUMENTS

| | | |
|---|---|---|
| 2,068,721 | 1/1937 | Wappler et al. |
| 2,691,370 | 10/1954 | Wallace . |
| 3,664,330 | 5/1972 | Deutsch . |
| 3,882,854 | 5/1975 | Hulka et al. . |
| 4,300,564 | 11/1981 | Furihata . |
| 4,471,766 | 9/1984 | Terayama . |
| 4,576,145 | 3/1986 | Tsuno et al. ........................... 600/156 |
| 4,588,294 | 5/1986 | Siegmund . |
| 4,616,631 | 10/1986 | Takahashi . |
| 4,620,547 | 11/1986 | Boebel . |
| 4,651,201 | 3/1987 | Schoolman . |
| 4,656,999 | 4/1987 | Storz . |
| 4,759,348 | 7/1988 | Cawood . |
| 4,770,163 | 9/1988 | Ono et al. ............................ 600/156 |
| 4,782,819 | 11/1988 | Adair . |
| 4,867,529 | 9/1989 | Utsumi et al. . |
| 5,016,098 | 5/1991 | Cooper et al. . |
| 5,127,393 | 7/1992 | McFarlin et al. ..................... 600/114 |
| 5,147,356 | 9/1992 | Bhatta . |
| 5,152,779 | 10/1992 | Sanagi . |
| 5,197,457 | 3/1993 | Adair .................................. 600/114 |
| 5,230,621 | 7/1993 | Jacoby . |
| 5,263,928 | 11/1993 | Trauthen et al. ..................... 600/156 |
| 5,281,134 | 1/1994 | Schultz . |
| 5,312,400 | 5/1994 | Bales et al. . |
| 5,373,840 | 12/1994 | Knighton . |
| 5,512,034 | 4/1996 | Finn et al. . |
| 5,667,472 | 9/1997 | Finn et al. ........................... 600/104 |
| 5,667,473 | 9/1997 | Finn et al. ........................... 600/104 |

FOREIGN PATENT DOCUMENTS

| | | |
|---|---|---|
| A-0 316 816 | 5/1989 | European Pat. Off. . |
| A-20 24 195 | 11/1970 | Germany . |
| U-86 00 868 | 3/1986 | Germany . |
| A-86 00 848.4 | 4/1986 | Germany . |
| 39 20 706-A1 | 6/1989 | Germany . |
| WO 94/14368 | 2/1993 | WIPO . |
| PCT/US92/ 07857 | 4/1993 | WIPO . |
| PCT/US92/ 09564 | 5/1994 | WIPO . |
| PCT/US92/ 09616 | 5/1994 | WIPO . |

OTHER PUBLICATIONS

"Fourth Annual Course On Minimally Invasive Therapy Of The Brain", dated Aug. 25–27, 1994, and presented at Loew's Hotel in Santa Monica, California.

*Primary Examiner*—John P. Leubecker
*Attorney, Agent, or Firm*—Olson & Hierl, Ltd.

[57] ABSTRACT

The present invention is a surgical instrument for use with a viewing system and, if desired, an irrigation fluid supply system. The surgical instrument can be readily assembled and includes an elongated shaft and a flexible endoscope or optical assembly that can be readily and removably secured along substantially the entire length of the shaft by a mounting tube or other mounting means.

59 Claims, 11 Drawing Sheets

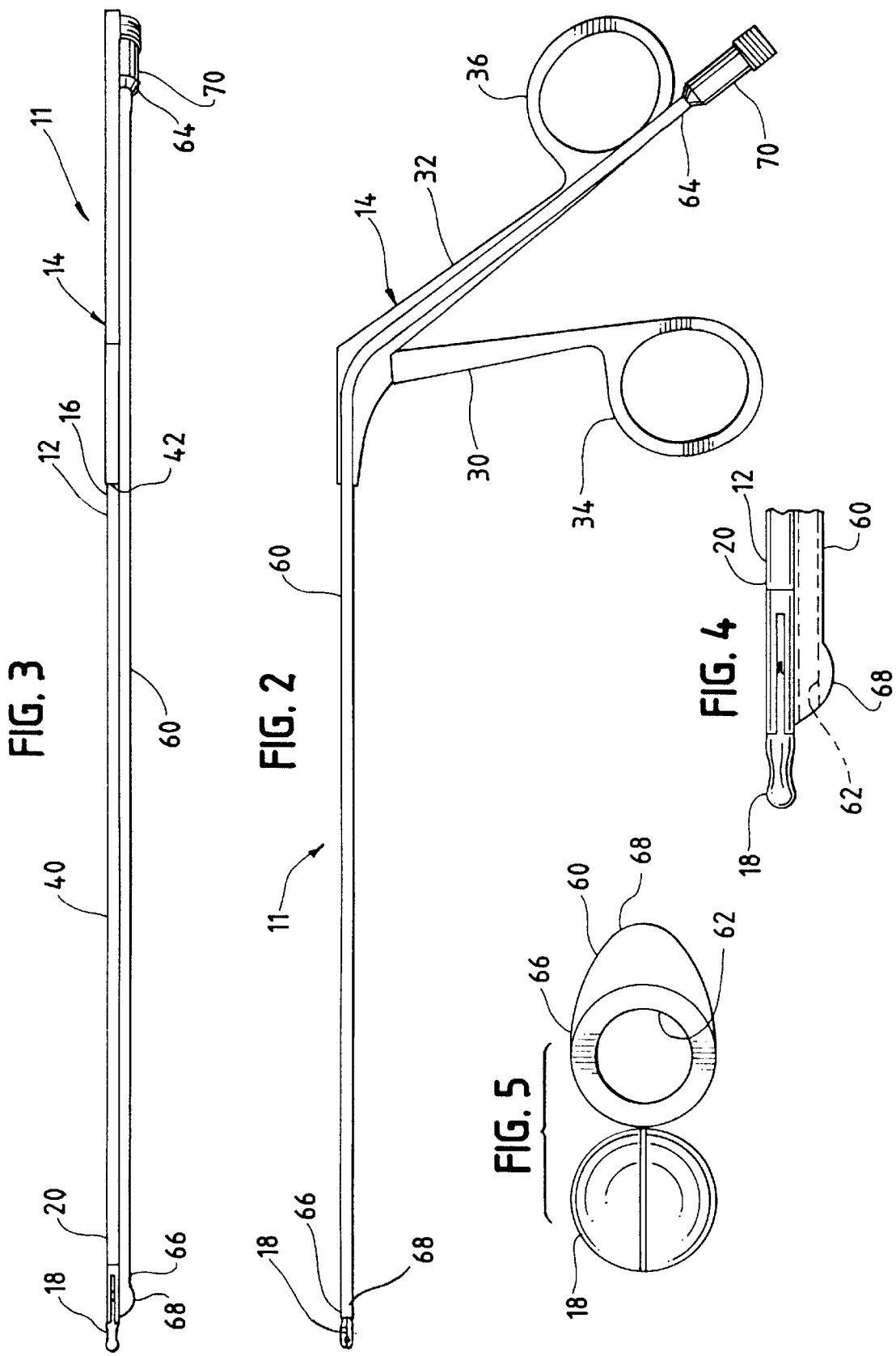

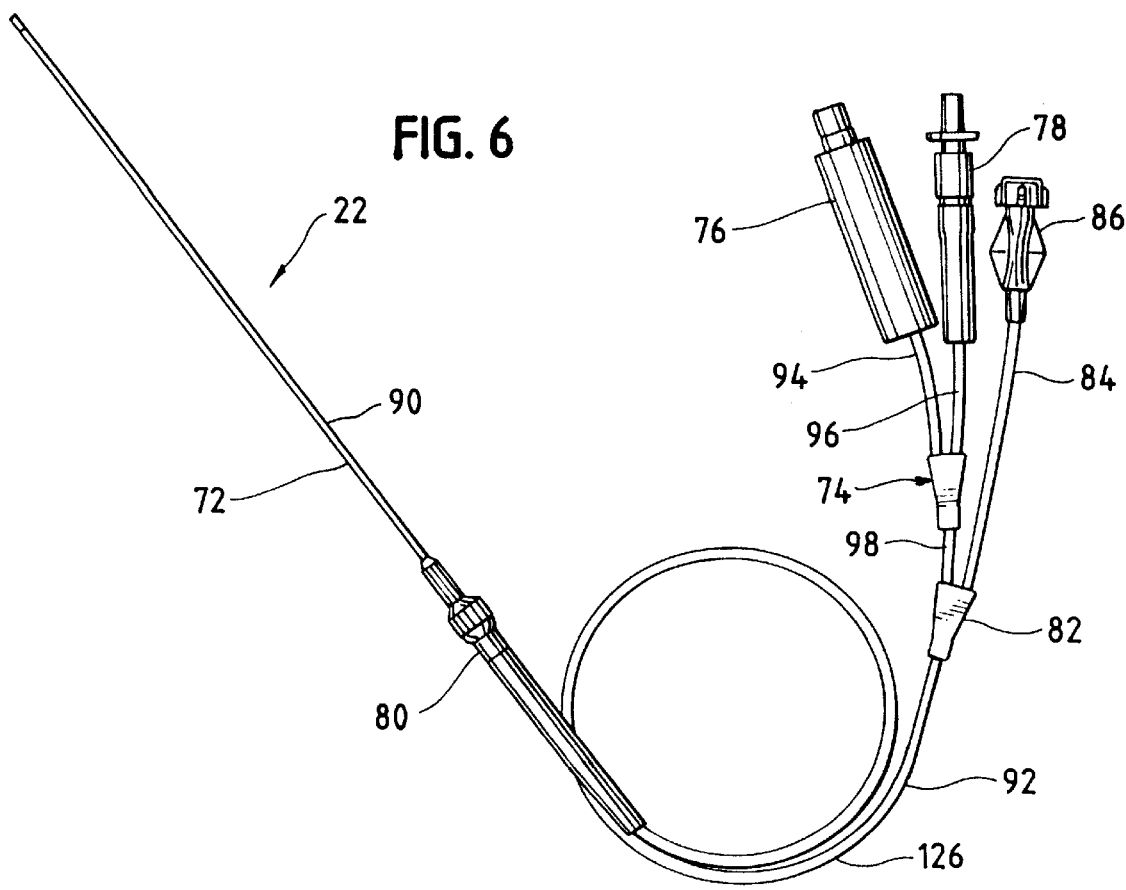
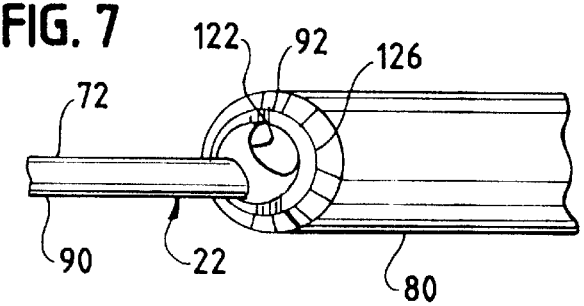
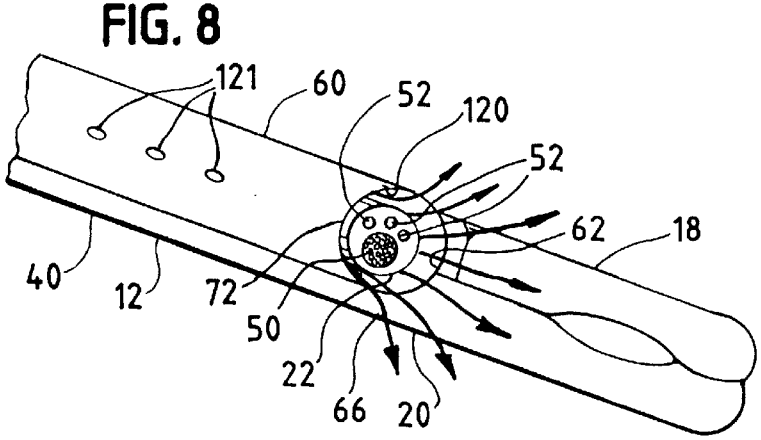

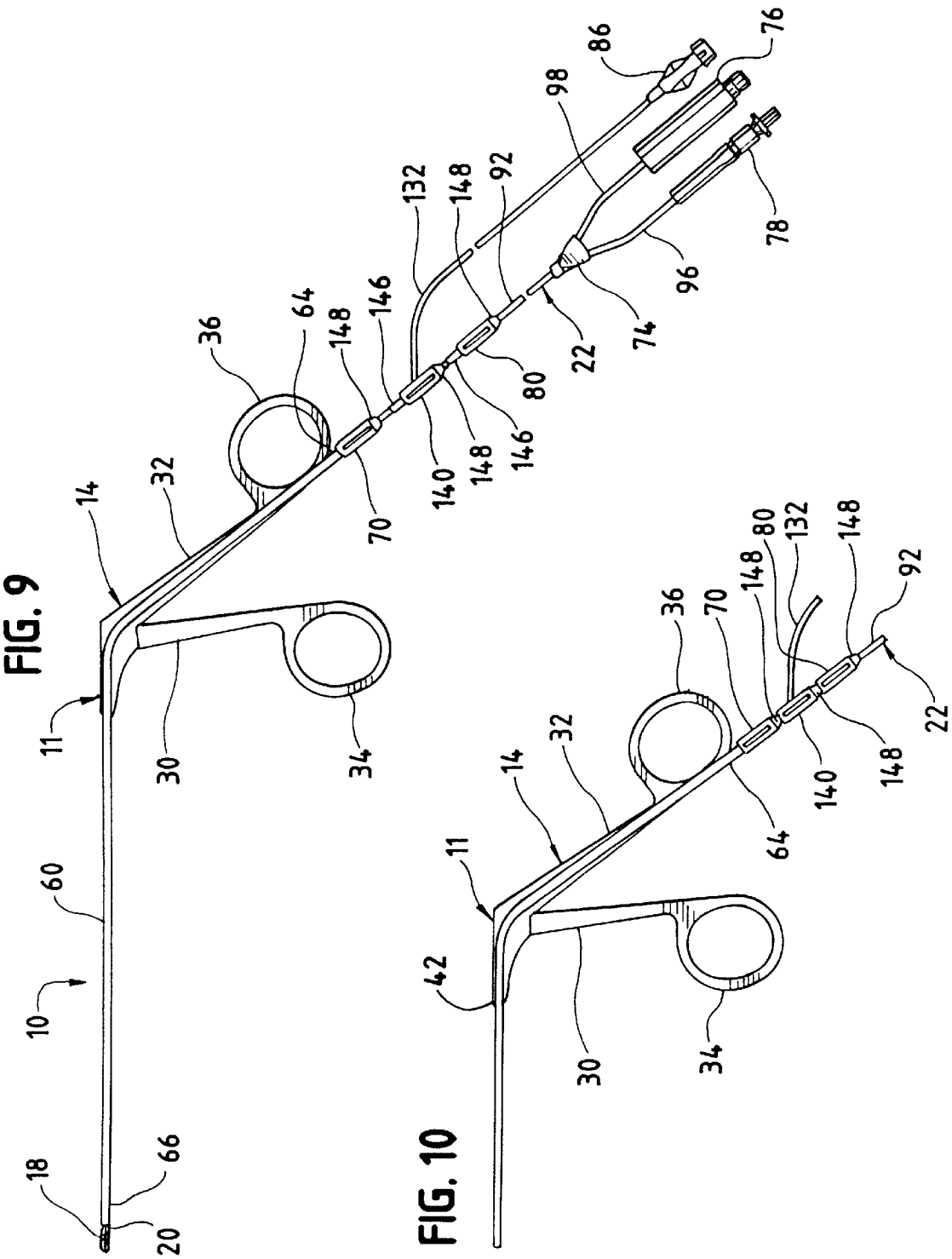

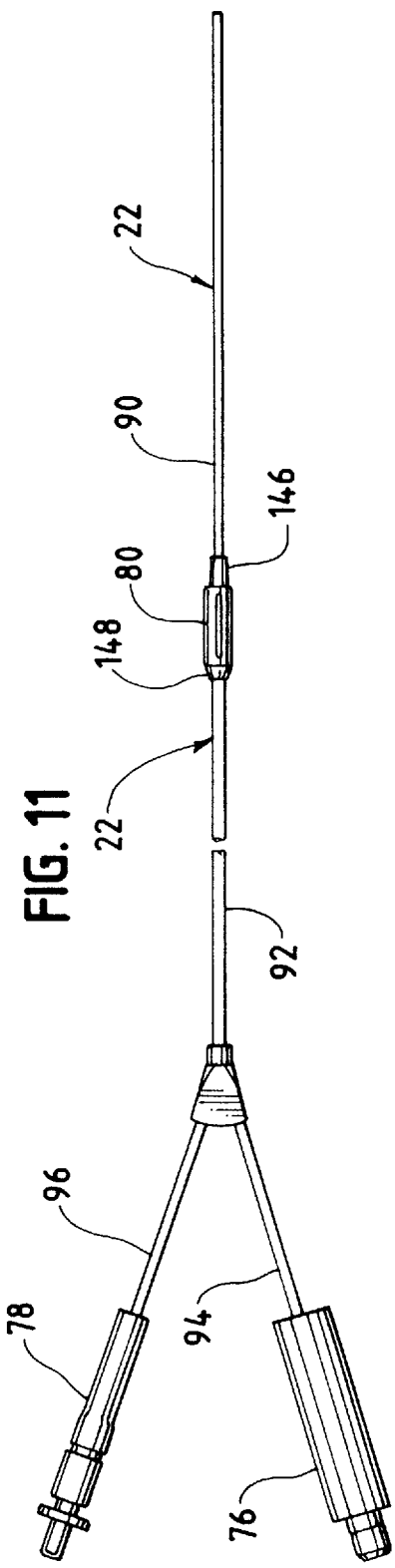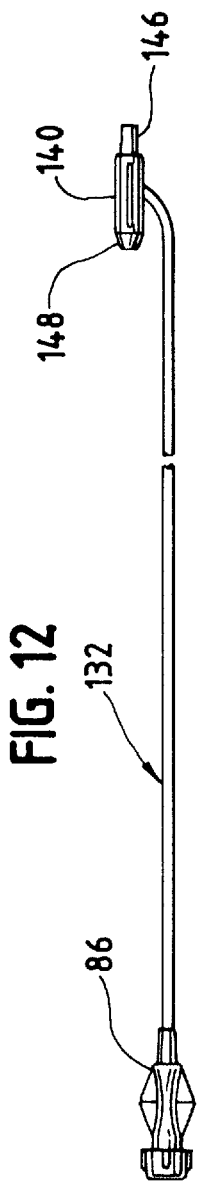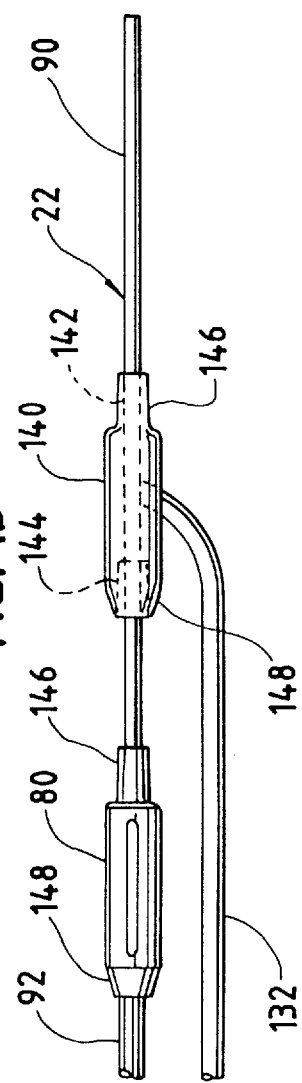

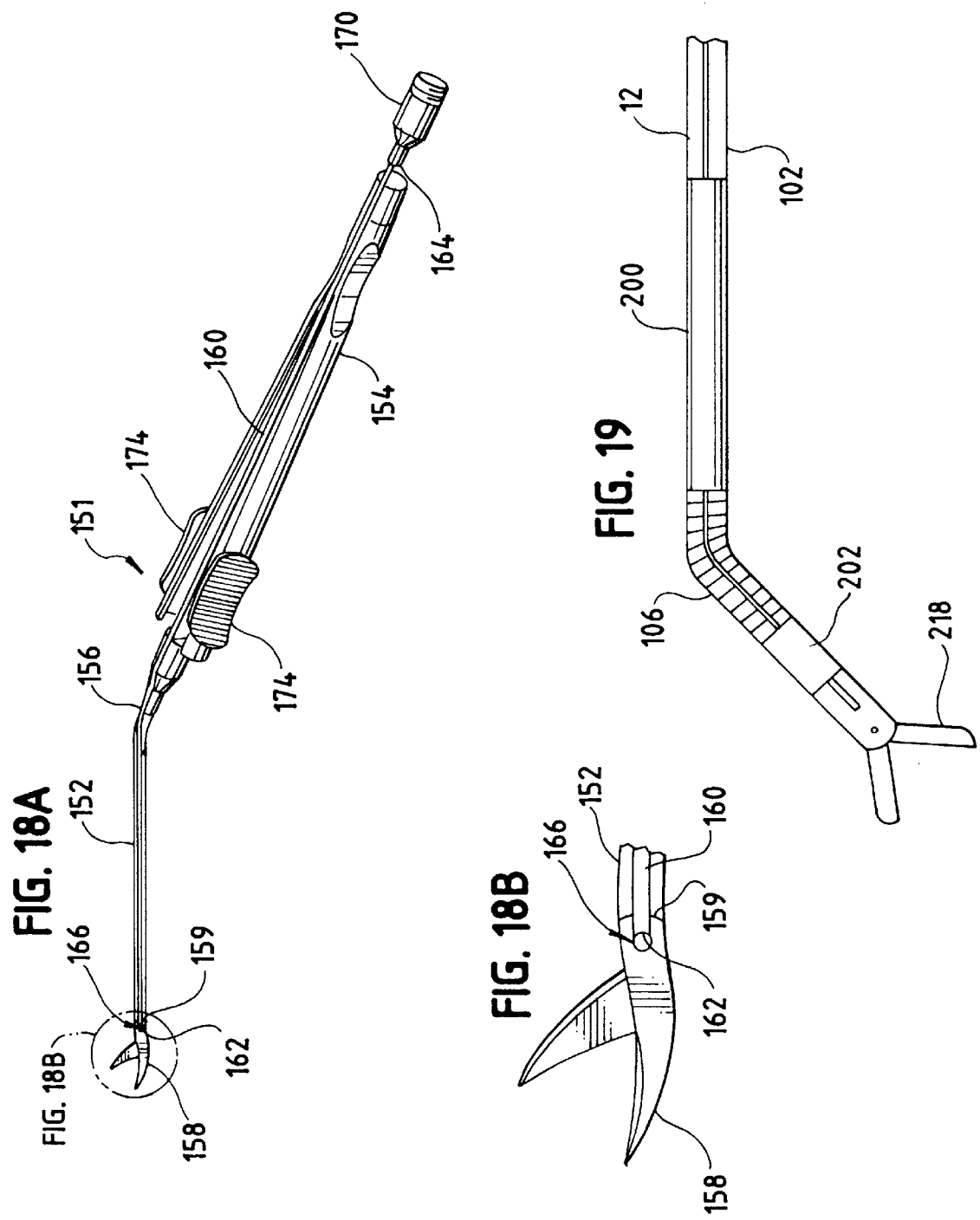

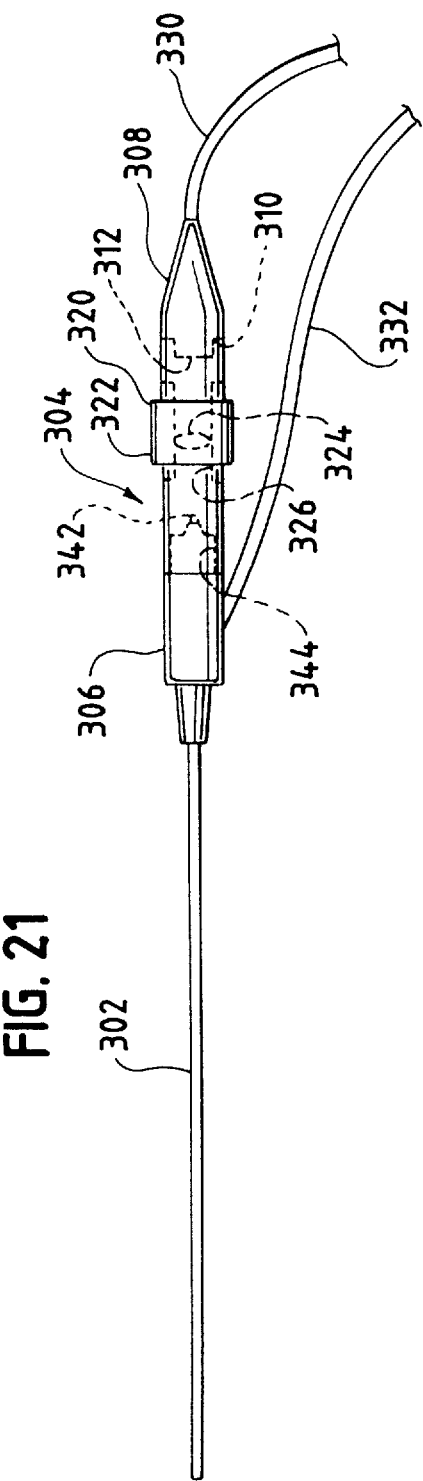
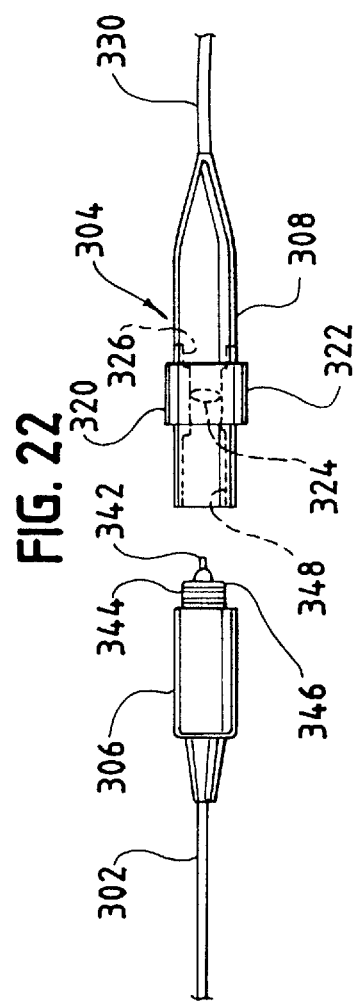
FIG. 21
FIG. 22

SURGICAL INSTRUMENT FOR USE WITH A VIEWING SYSTEM

This application is a continuation-in-part of U.S. patent application Ser. No. 08/472,187, filed Jun. 7, 1995 now U.S. Pat. No. 5,667,473.

TECHNICAL FIELD OF THE INVENTION

The present invention relates generally to surgical instruments having optical assemblies.

BACKGROUND OF THE INVENTION

Instruments having endoscopic or optical assemblies have been extensively used by surgeons to provide an internal view of an organ, body passage or lumen of a patient during a surgical procedure. Such instruments usually include working elements, such as forceps, scissors, probes and the like, to enable the surgeon to manipulate body tissue during the surgical procedure. Such instruments have been used in a wide range of surgical and microsurgical procedures including, for example, operations on small intracranial vessels, extirpation on small pituitary adenomas, low-risk clipping of intracranial aneurysms, removal of extensive pituitary adenomas with conservation of the infundibulum and the small hypothalamic vessels as well as the preservation of the facial nerve, and preservation of the cochlear nerve in connection with extirpation of acoustic neuromas.

There are, however, drawbacks associated with the use of surgical instruments having endoscopic assemblies. For example, the endoscopes tend to interfere with the surgical procedure and affect the control and tactile feel imparted by the instrument to the surgeon. Additionally, the endoscope may be difficult to remove or replace, and, as a result, the surgical instrument may have a limited life and may be difficult and costly to sterilize.

For example, surgical instruments have been used that include endoscopes having channels that receive the surgical tools. Such instruments tend to be large and difficult to work with, however. The instruments are difficult to control and the tactile feel of the tools is significantly affected by the endoscopes.

Surgical instruments that have the endoscopes mounted within the shaft of the instrument often tend to be relatively large in diameter which limits their use. Since the endoscope cannot be removed, the entire instrument must be replaced if the endoscope becomes damaged. Also, it is likely that the instrument cannot be heat sterilized since endoscopes can be damaged by exposure to heat.

Those surgical instruments that include an endoscope attached to the exterior of the shaft of the instrument tend to be awkward because the endoscopes protrude from the shaft of the instrument and tend to interfere with the surgical procedure and limit the surgeon's ability to move or twist the instrument during surgery. Also, because precise alignment is required between the endoscope and the working element, the endoscope cannot be replaced quickly and easily if it becomes damaged or if the instrument is being heat sterilized.

Additionally, rigid endoscopes are often used which are difficult to work with and expensive to manufacture because the instruments require precise alignment of the endoscope. Since surgical instruments with rigid endoscopes cannot be bent, they also limit the surgeon's ability to gain access to many areas of the body to be worked on.

Although it is known to use flexible endoscopes to enable access to parts of the body that are not accessible with rigid instruments, it often is difficult to position the working end of the instrument due to the construction of the device. A surgical instrument having a distal end that cannot be precisely maneuvered tends to interrupt a surgeon's tactile feel and ability to control the working element of the instrument and the tissue being manipulated.

For many of the same reasons described above, surgical instruments having irrigation systems also have limitations. Irrigation systems tend to interfere with the surgical procedure and affect the control and tactile feel of surgical instruments because they tend to protrude from the instrument and impose forces on the instruments.

Accordingly, what is needed is a surgical instrument having an optical assembly that does not interfere with the surgical procedure and does not substantially affect the control and tactile feel of the instrument. Such an instrument should provide improved viewing of the surgical procedure. The optical assembly should also preferably be readily and removably secured to a shaft of the instrument so that the instrument can be assembled readily and easily and so that the optical assembly can be removed or replaced readily and easily. The optical assembly also should be flexible to facilitate quick and easy assembly, even if the handle of the instrument is offset relative to the shaft or if the shaft is curved. The device should also be small in cross section to provide for easy access to the tissue and improved tactile feel. Desirably, the device also should preferably include a convenient irrigation means for providing an irrigation fluid to the surgical area. The present invention meets these desires.

SUMMARY OF THE INVENTION

The present invention relates to a surgical instrument that can be readily assembled and that includes an elongated shaft and a flexible endoscope or optical assembly that can be readily and removably secured along substantially the length of the shaft. The surgical instrument is used with a viewing system and, if desired, an irrigation fluid supply system for supplying an irrigation fluid to a distal portion of the instrument.

In a preferred embodiment of the invention, the surgical instrument also includes a working element mounted on a distal end of the shaft, and a handle mounted on a proximal end of the shaft. The handle includes a gripping portion which is held by a surgeon while using the instrument. The endoscope includes one or more image fiber bundles and one or more illumination fibers contained within the endoscope. The handle may be offset relative to the shaft, and the shaft may be substantially linear, bent, curved, rigid, flexible, bendable or malleable by a user of the instrument.

Preferably, a mounting tube that defines a longitudinal bore is secured along the exterior of the shaft and the gripping portion of the handle for removably securing the endoscope to the shaft and the handle. The mounting tube can extend from a proximal end of the handle to or near the distal end of the shaft. The mounting tube may be rigid, bendable, or malleable, or may have a predetermined bend or curve. A first connector is secured to a proximal end of the mounting tube, extending proximally of the handle. In one embodiment, the first connector is one part of a two-part fitting, such as a luer connector or an SMA connector.

The endoscope includes a sheath or case substantially encasing the image fiber bundle and illumination fibers along substantially the entire length of the endoscope. A second connector is mounted on the endoscope and is located proximal of a distal end of the endoscope to define a working or distal portion and a proximal portion of the endoscope. In accordance with one embodiment of the invention, the second connector is the other part of the two-part fitting, and the first and second connectors are attachable to each other so that the distal portion of the endoscope is received within the longitudinal bore of the mounting tube. The instrument may include a coupling device for coupling the proximal end of the image fiber bundle or endoscope to the viewing system.

The endoscope in accordance with the invention does not interfere with the surgical procedure and does not significantly affect the control or tactile feel of the surgical instrument. The endoscope can be readily assembled on the shaft of the instrument or readily removed or replaced even if the handle of the instrument is offset relative to the shaft, if the shaft is flexible, bendable or malleable, or if the shaft has a predetermined curve or bend.

The surgical instrument may also include an irrigation means, which is in fluid flow communication with the irrigation fluid supply system, for providing the irrigation fluid to a distal end of the endoscope. In one embodiment, an irrigation passageway is defined within the longitudinal bore of the mounting tube by the endoscope and the mounting tube through which the irrigation fluid may be transferred. This embodiment is particularly advantageous because it is adapted to transfer irrigation fluid along the shaft of the surgical instrument without adding structure. Because the irrigation passageway is defined within the mounting tube, the irrigation means of this embodiment does not add structure along the length of the shaft and, thus, does not interfere with the surgical procedure. The irrigation means in accordance with this embodiment also facilitates re-useability of the endoscope.

If desired, the irrigation passageway may be in fluid flow communication with an irrigation channel defined in the proximal portion of the endoscope or with an irrigation tube that is separate from the endoscope and joined to the proximal end of the mounting tube. The irrigation tube may be joined to the proximal end of the mounting tube by a connector assembly.

Alternatively, the irrigation means may include an irrigation channel defined by the endoscope that extends substantially the entire length of the endoscope. The endoscope containing an irrigation channel that extends all or part of the length of the endoscope is generally intended to be disposable after a single use because the irrigation channel desirably has a relatively small diameter and thus is difficult to clean.

Other mounts can be included for removably mounting the endoscope to the shaft. For example, the instrument can include a proximal mount mounted to a proximal portion of the shaft and, preferably, the handle; and a distal mount mounted to a distal portion of the shaft. The handle may be offset relative to the proximal portion of the shaft. If desired, the proximal and distal portions may be offset relative to each other The proximal and distal mounts may be in the form of mounting tubes extending along the proximal and distal portions of the shaft. Alternatively, the proximal and distal mounts may each be a molded or shrinkable tubing adapted to form a secure compression fitting or shrinkable coupling, which is particularly useful for irregularly-shaped shafts. The tubing can be heat, water or chemically shrinkable. The proximal and distal mounts may be spaced or interconnected as a continuous mount.

The present invention also includes a method of retrofitting an existing surgical tool with the endoscope described above. The method starts with an existing surgical tool that includes a shaft having a proximal end and a distal end, a handle connected to the proximal end of the shaft and a working element connected to the distal end of the shaft. The handle is offset relative to the shaft, and includes a gripping portion. The mounting tube described above is secured to the shaft so that the mounting tube extends along substantially the entire length of the shaft and along substantially the entire length of the handle. The endoscope is removably mounted to the shaft by attaching together the connector secured to the endoscope and the connector secured to the mounting tube so that the distal portion of the endoscope is received within the mounting tube and extends along substantially the entire length of the shaft and along substantially the entire length of the handle and so that the endoscope can be used to view a portion of the working element.

A surgical instrument in accordance with the present invention provides numerous benefits. For example, the surgical instrument facilitates high-precision surgical procedures and improves the viewing of the surgical site without interfering with the surgical procedure or substantially affecting the control and tactile feel of the instrument. The instrument is smaller and easier to control than prior art instruments having endoscopes. The instrument can be assembled readily and easily. The endoscope can be removed or replaced readily and easily, even if the handle is offset, if the shaft is flexible, bendable or malleable, or if the shaft has a predetermined bend or curve. The invention allows the instrument to be heat sterilized without exposing the endoscope to heat. The invention also permits the separate sterilization of the endoscope, and re-sterilization of the endoscope for repeated uses. In addition, a new endoscope can be used when one becomes damaged without having to replace the entire instrument. The irrigation means of the present invention facilitates effective irrigation during the surgical procedure without interfering with the surgical procedure or significantly affecting the control and tactile feel of the instrument, and also can be readily assembled and used.

Another advantage of the present invention is that it permits use of a single endoscope with an entire set of surgical tools, such as a biopsy forceps, scissors, and grasping forceps. As a result, the surgeon can readily remove the endoscope after one surgical procedure has been accomplished and reassemble it on another tool to begin another surgical procedure. The interchangeability of the endoscope with other tools results in convenience to the surgeon and also in cost savings because a single endoscope can be used to accomplish several procedures.

Numerous other features and advantages of the present invention will become readily apparent from the detailed description of the invention, the accompanying drawings and the appended claims.

BRIEF DESCRIPTION OF THE DRAWINGS

FIG. 2 is a side elevational view of a surgical tool of the surgical instrument of FIG. 1, including a shaft, handle, mounting tube and working element;

FIG. 3 is a top view of the surgical tool of FIG. 2;

FIG. 4 is an enlarged top view of a distal end of the surgical tool of FIGS. 2 and 3;

FIG. 5 is an enlarged end view of the distal end of the surgical tool of FIGS. 2–4;

FIG. 6 is a side elevational view of an endoscope of the surgical instrument of FIG. 1;

FIG. 7 is an enlarged view of the endoscope of FIG. 6 taken near a distal end of a connector of the endoscope illustrating an irrigation channel defined in a proximal portion of the endoscope that terminates at the distal end of the connector;

FIG. 8 is a broken perspective view of the distal end of the surgical instrument of FIG. 1 illustrating with arrows an irrigation fluid passing from a distal end of a mounting tube;

FIG. 9 is a side elevational view of a further embodiment of the surgical instrument, illustrating an irrigation tube and a connector or luer assembly for securing an irrigation tube to a mounting tube and an endoscope and illustrating the luers in an aligned, but unengaged, position;

FIG. 10 is a broken side elevational view of the surgical instrument of FIG. 9, illustrating the luers in an engaged position;

FIG. 11 is a side elevational view of the endoscope of the surgical instrument of FIGS. 9 and 10 including one of the luers mounted to the endoscope;

FIG. 12 is a broken view of the irrigation tube assembly of the surgical instrument of FIGS. 9 and 10 including another one of the luers mounted to a distal end of the irrigation tube;

FIG. 13 is a broken side elevational view of the irrigation tube assembly of FIG. 12 and the endoscope of FIG. 11, illustrating the luer mounted on the distal end of the irrigation tube receivingly engaging a distal portion of the endoscope and illustrating with dashed lines a longitudinal channel defined by the luer of the irrigation tube assembly and a bore adapted to receive the luer of the endoscope;

FIG. 18 is a perspective view of a surgical scissors instrument in accordance with a further embodiment of the invention, with an enlarged view of a distal end of the instrument;

FIG. 19 is a side elevational view of a shaft and handle of the surgical instrument in accordance with a further embodiment of the invention;

FIG. 21 is a side elevation view of an endoscope and a CCD camera head assembly in accordance with an embodiment of the invention similar to the embodiment of FIG. 20; and FIG. 22 is a broken view illustrating the endoscope, the camera head assembly and means for securing together the endoscope and the CCD camera head assembly in accordance with the embodiment of FIG. 21.

DETAILED DESCRIPTION OF THE PREFERRED EMBODIMENTS

Figure 1:
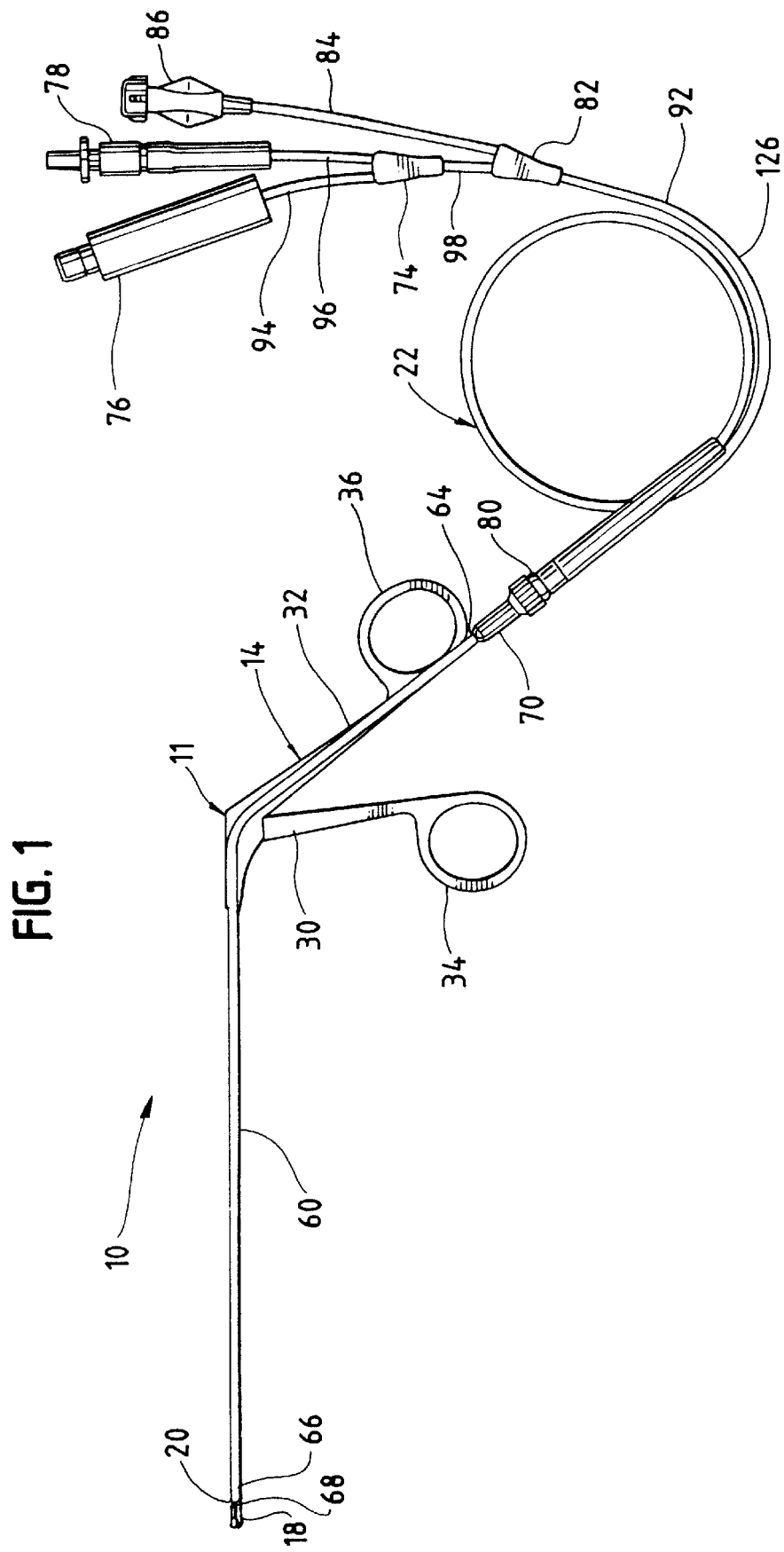
FIG. 1 is a side elevational view of an embodiment of a surgical instrument in accordance with the invention.

A surgical instrument 10 in accordance with a preferred embodiment of the present invention is shown in FIGS. 1–8. The surgical instrument 10 includes a tool 11 having an elongated shaft 12 with a handle 14 mounted on a proximal end 16 of the shaft, and a working element 18 mounted on a distal end 20 of the shaft. The surgical instrument 10 also includes an optical assembly which preferably is in the form of a flexible endoscope 22. The handle 14 has a portion that is intended to be gripped or held by a surgeon so that the working element can be used to manipulate tissue during a surgical procedure.

In the embodiment shown in FIGS. 1–8, the handle 14 is offset relative to the shaft 12, and includes a first handle member 30 that is pivotally connected to a second handle member 32. The handle members 30 and 32 terminate in respective finger receiving loops 34 and 36. The handle members 30 and 32 and the loops 34 and 36 form the gripping portion of the handle 14. The endoscope 22 extends from the handle gripping portion, such as either above the loop 36 or below the loop 36 as shown.

The working element 18 is rigidly secured to the distal end 20 of the shaft 12 in any suitable manner. In the embodiments of FIGS. 1–17, the working element 18 is in the form of forceps. The working element 18 instead, however, may include a scissors (see FIGS. 18–19), knife, probe, or coagulator, electrosurgical electrodes, or any other suitable tool.

The shaft 12 may be in the form of a tube 40 with its proximal end fitted into a bore 42 defined in the second handle member 32 (see, e.g., FIG. 3). The shaft 12 may be straight or have a predetermined bend or curve along its axis. The shaft 12 may be rigid. It may be flexible, bendable or malleable so that it may be adjusted by the surgeon. For example, the shaft may have a distal portion that is displaceable to alternative positions wherein the distal portion does not have the same axis as a proximal portion of the shaft.

The shaft 12 may also include an actuating mechanism operably coupled to the working element 18 to operate the working element. An actuating rod or cable may be affixed to the upper end of the first handle member 30 and extend through a lumen defined by the tube 40 to join the movable forceps 18. The shaft 12 may be constructed of a stainless steel or any other suitable material.

With this embodiment, by grasping the handle members 30 and 32 by their respective finger-receiving loops 34 and 36, and by pivoting the first handle member 30 back and forth relative to the stationary second handle member 32, the rod or cable moves reciprocally within the tube 40 to cause the forceps or working element 18 to open and close in a scissors-like action.

Figure 16:
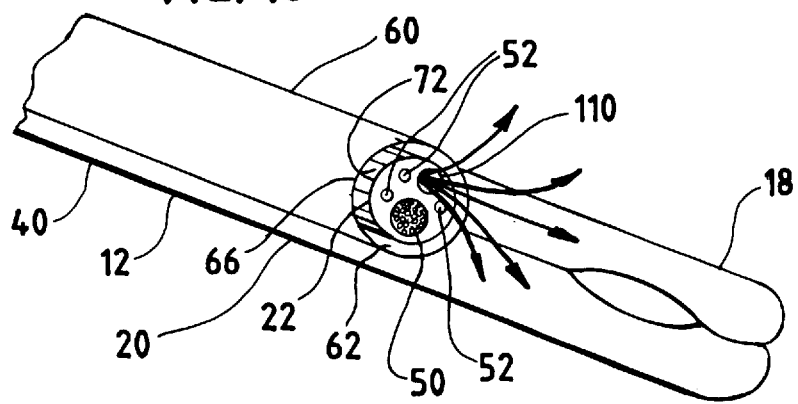
FIG. 16 is a broken perspective view of a distal end of the surgical instrument illustrating a distal end of a mounting tube and an alternative embodiment of the endoscope defining an irrigation channel that terminates at its distal end and illustrating with arrows an irrigation fluid passing from the irrigation channel.

The flexible endoscope 22 preferably includes at least one image fiber bundle 50 to permit viewing by a surgeon and one or more illumination fibers 52 (see, e.g., FIGS. 8 and 16). An objective lens is mounted on a distal end of the image fiber bundle 50 for defining a field of view which includes at least part of the working element 18, and to focus the light rays reflected from the illuminated surgical site onto the plane occupied by the distal end of the image fiber bundle.

In a preferred embodiment, a mounting tube 60 is affixed to the exterior of the shaft 12 and the handle 14, extending along substantially the entire length of the shaft 12 and handle 14 from a proximal end of the handle to near the working element 18. The mounting tube 60 may be affixed to the shaft 12 and handle 14 in any suitable manner, such as, for example, by solder, welding or any suitable bonding agent. The mounting tube 60 is illustrated as being affixed to the side or laterally of the shaft 12 relative to the handle 14. The mounting tube 60 defines a longitudinal bore 62 extending between a proximal end 64 and a distal end 66 of the mounting tube. Alternatively, all or part of the mounting tube 60 and bore 62 may be defined by the handle 14 or shaft 12. The distal end 66 of the mounting tube 60 may define a bulbous atraumatic tip 68 to enhance the tactile response of the instrument 10 and to eliminate sharp edges.

The mounting tube 60 may have a predetermined curve or bend to accommodate the offset handle 14 or any curves or bends in the shaft 12 or handle or so that the distal end of the endoscope 22 is positioned at a predetermined angle relative to the working element 18. The mounting tube 60 may be rigid. The mounting tube 60 may be bendable or malleable to accommodate a bendable or malleable shaft so that the surgical instrument 10 can be used to reach areas that may be difficult for the surgeon to reach. The bendable or malleable mounting tube 60 also permits the surgeon to position the distal end of the endoscope 22 at a desired angle relative to the working element 18 and thereby adjust the viewing area of the endoscope. A malleable shaft 12 and tube 60 is most preferred because it allows the surgeon to adjust the tool 11 to have a particular shape or bend and the chosen shape is retained.

The mounting tube may be constructed of any suitable material, such as, for example, stainless steel. A first connector 70 is mounted at the proximal end 64 of the mounting tube 60, extending proximally of the handle 14, for removably securing the endoscope 22 to the mounting tube, as described below.

The shaft 12 and mounting tube 60 preferably are each adapted and constructed to have a small outside diameter such that the instrument 10 can be passed through an introducer, a cannula or directly into a narrow lumen or small surgical incision and still have a sufficient length to allow the working element 18 to reach the organ or tissue to be manipulated or cut. In a preferred embodiment, the outer diameters of the shaft 12 and the mounting tube 60 are approximately 1.3 mm and 1.75 mm, respectively, and the distance between a distal end of the working element 18 and the proximal end 16 of the shaft is approximately 15 cm.

The flexible endoscope 22 includes a case or sheath 72 substantially along its length for encasing the image fiber bundle 50 and the illumination fibers 52. The sheath 72 may be made of any suitable material that preferably is flexible such as, for example, a plastic or rubber tubing. The illumination fibers 52 extend through a hub member 74 to an illumination fiber tube segment 94, and to a terminal connector 76 that is adapted to mate with a jack of suitable light source. Similarly, the image fiber bundle 50 passes through the hub member 74, to an image fiber bundle tube segment 96, and to a terminal connector 78 that is adapted to mate with an image input of a suitable viewing system or device such as a video unit or direct viewing optics.

In the preferred embodiment, the endoscope 22 includes a second connector 80 mounted on the endoscope proximal of the distal end of the endoscope. The second connector 80 defines an endoscope working or distal portion 90 that extends distally of the second connector and a proximal portion 92 (see, e.g., FIGS. 6, 11 and 15). The distal portion 90 of the endoscope 22 is inserted into the longitudinal bore 62 of the mounting tube 60 and slidingly receivable by the mounting tube until the second connector 80 comes into contact with the first connector 70. The two connectors 70 and 80 are then matingly engaged, releasably locking the endoscope 22 and the mounting tube 60 together so that substantially the entire distal portion 90 of the endoscope extends within the longitudinal bore 62 of the mounting tube. In the preferred embodiment, when the endoscope 22 and the mounting tube are joined together, the distal portion 90 of the endoscope 22 and the atraumatic bulbous tip 68 are substantially co-terminus at their respective distal ends, or the distal end of the endoscope 22 is spaced proximally of the distal end of the atraumatic bulbous tip a predetermined distance.

The first and second connectors 70 and 80 may each be one part of a two-part fitting, such as luers or male and female SMA connectors (with, for example, the female part of the SMA connector mounted to the mounting tube and the male part of the SMA connector mounted on the endoscope 22). The distal portion 90 of the endoscope 22 and the mounting tube 60 can be designed with very precise tolerances to correctly position the distal end of the endoscope 22 with respect to the working element 18.

As illustrated by the embodiment of FIGS. 1–8, the distal portion 90 of the endoscope 22 is slidably received within the mounting tube 60 and the endoscope is secured to the mounting tube only at the proximal end 64 of the mounting tube. Since the distal portion 90 of the endoscope 22 is not secured to the mounting tube along the length of the mounting tube 60, the mounting tube can be bent by the surgeon without causing undue stress to the endoscope which may damage or break the image fibers.

As shown in FIGS. 1–8, the surgical instrument 10 in accordance with a preferred embodiment of the invention desirably includes an irrigation means for providing an irrigation fluid to or near the distal end 66 of the mounting tube 60. The irrigation fluid is used to maintain a clear view through the endoscope 22.

With this embodiment, an irrigation passageway 120 is defined within the longitudinal bore 62 of the mounting tube 60 by the distal portion 90 of the endoscope 22, through which the irrigation fluid is transferred. As illustrated in FIG. 8, if desired, one or more apertures 121 may be defined on the mounting tube 60 to provide additional outlets for the irrigation fluid and to relieve the fluid pressure of the irrigation fluid or tissue at the distal end 66 of the mounting tube 60. In a preferred embodiment, the inner diameter of the mounting tube is approximately 1.5 mm and the outer diameter of the distal portion of the endoscope is approximately 1.0 mm.

The irrigation passageway 120 is particularly advantageous because it is adapted to transfer irrigation fluid along the shaft 12 of the surgical instrument 10 and outside the endoscope without adding to the size of the instrument. The irrigation means of this embodiment does not add structure along the length of the shaft because the passageway is defined within the mounting tube. Thus, the irrigation means does not interfere with the surgical procedure or significantly affect the control and tactile feel of the instrument. The irrigation passageway also facilitates re-useability of the endoscope.

The irrigation passageway 120 is in fluid flow communication with the irrigation fluid supply system by, for example, an irrigation channel 122 that is defined by the proximal portion 92 of the endoscope 22 (see FIG. 7). The irrigation channel 122 extends within the proximal portion 92 of the endoscope, from a distal end of the second connector 80 and passes through a hub member 82, to an irrigation tube segment 84, and to an irrigation tube connector 86 that is attachable to an irrigation fluid supply system for providing the irrigation fluid. A segment 98 of the endoscope 22 that includes the image fiber bundle 50 and illumination fibers 52 extends from the hub member 82 to the hub member 74. The irrigation channel 122 may be defined by an irrigation tube contained within the proximal portion of the endoscope. As illustrated by the arrows in FIG. 8, the irrigation fluid passes through the longitudinal bore 62 between the mounting tube and the distal portion 90 of the endoscope 22.

As shown in FIGS. 6 and 7, the endoscope includes a second sheath or case 126 that extends along the proximal portion 92 of the endoscope 22, terminating at or near the distal end of the second connector 80. The second sheath 126 encases the sheath 72 and the irrigation channel 122 along the proximal portion of the endoscope 22. The irrigation channel 122 runs from the hub member 82 to the distal end of the second connector 80 so that the irrigation fluid can pass from the irrigation channel to the irrigation passageway 120 when the first and second connectors 70 and 80 are mated (see, e.g., FIG. 7 and generally FIG. 1). An epoxy can be used to fill the space between the irrigation channel 122, the sheath 72 and the second sheath 126 within the proximal portion 92 of the endoscope 22.

Alternatively, as shown in FIGS. 9–13, the irrigation passageway 120 may be in fluid flow communication with the irrigation fluid supply system by a separate irrigation tube 132 that is not contained within the endoscope 22 and that is joined to the proximal end 64 of the mounting tube 60 in any suitable manner. With this embodiment, the irrigation fluid also passes through the longitudinal bore 62 between the mounting tube 60 and the endoscope 22.

In the embodiment of FIGS. 9–13, the irrigation tube 132 is joined to the proximal end 64 of the mounting tube 60 by an assembly that includes three connectors, which preferably are in the form of three matingly-engageable luers. The irrigation tube 132 extends proximally of the handle 14 to the irrigation tube connector 86.

With this embodiment, a center connector 140 is joined to a distal end of the irrigation tube 132 that is matingly engageable with the first connector 70 on the mounting tube 60 and the second connector 80 on the endoscope 22. As shown in FIG. 13, the center connector 140 includes proximal and distal ends and defines a longitudinal channel 142 extending between the proximal and distal ends, with which the irrigation tube 132 is in fluid flow communication. The irrigation tube 132 preferably has a slight bend near its distal end, and is joined to the center connector 140 approximately half way along the length of the center connector. The center connector 140 defines a seat or bore 144 at its proximal end for receivingly engaging the second connector 80 and for providing a pressure fit. Preferably, the longitudinal channel 142 is adapted to receive the distal portion 90 of the endoscope 22 so that the center connector 140 can slidingly engage the distal portion 90 of the endoscope 22 prior to attachment of the connectors. Thus, the center connector 140 can be slid along the distal portion 90 of the endoscope 22, and then engaged with the second connector 80 to attach together the irrigation tube 132 and the endoscope.

As illustrated in FIG. 10, when engaged, the three connectors 70, 80, 140 join together the irrigation tube 132, the mounting tube 60 and the endoscope 22 so that the irrigation fluid passes from the irrigation tube 132 to the longitudinal bore 62 of the mounting tube 60. A sealing relationship is provided between the center connector 140 and the first and second connectors 70 and 80 so that all the irrigation fluid passes from the irrigation tube 132 to the irrigation passageway 120. Additionally, the length of the center connector is such that when the endoscope 22 is engaged with the surgical tool 11 the endoscope and the atraumatic bulbous tip 68 are substantially co-terminus at their respective distal ends, or the distal end of the endoscope 22 is spaced proximally of the distal end of the atraumatic bulbous tip a predetermined distance.

The three connectors 70, 80, 140 are illustrated in FIGS. 9–13 as being luers. The second and third luers or connectors 80, 140 are joined together by a cylindrical lip 146 defined by a distal end of the second luer 80, which is adapted to be received snugly within the bore 144 of the third luer 140 and engage the third luer by a pressure fit. Similarly, the third luer 140 includes cylindrical lip 146 at its distal end that is adapted to be received within a bore defined in the first luer 70 and engage the first luer by a pressure fit. In the illustrated embodiments, the luers 70, 80 and 140 include a tapered portion 148 at their proximal ends to facilitate engagement.

The center connector 140 can be used without the first connector 70 or the second connector 80. For example, the center connector 140 may engage directly the mounting tube 160 or the endoscope by any suitable manner, such as, for example, a threading engagement. If desired, the connector assembly may be used with surgical instruments that do not include a mounting tube, or that include an endoscope extending through the handle and shaft. Additionally, a center connector 140 that is not mounted to an irrigation tube can be used to engage the mounting tube with the endoscope.

Figure 14:
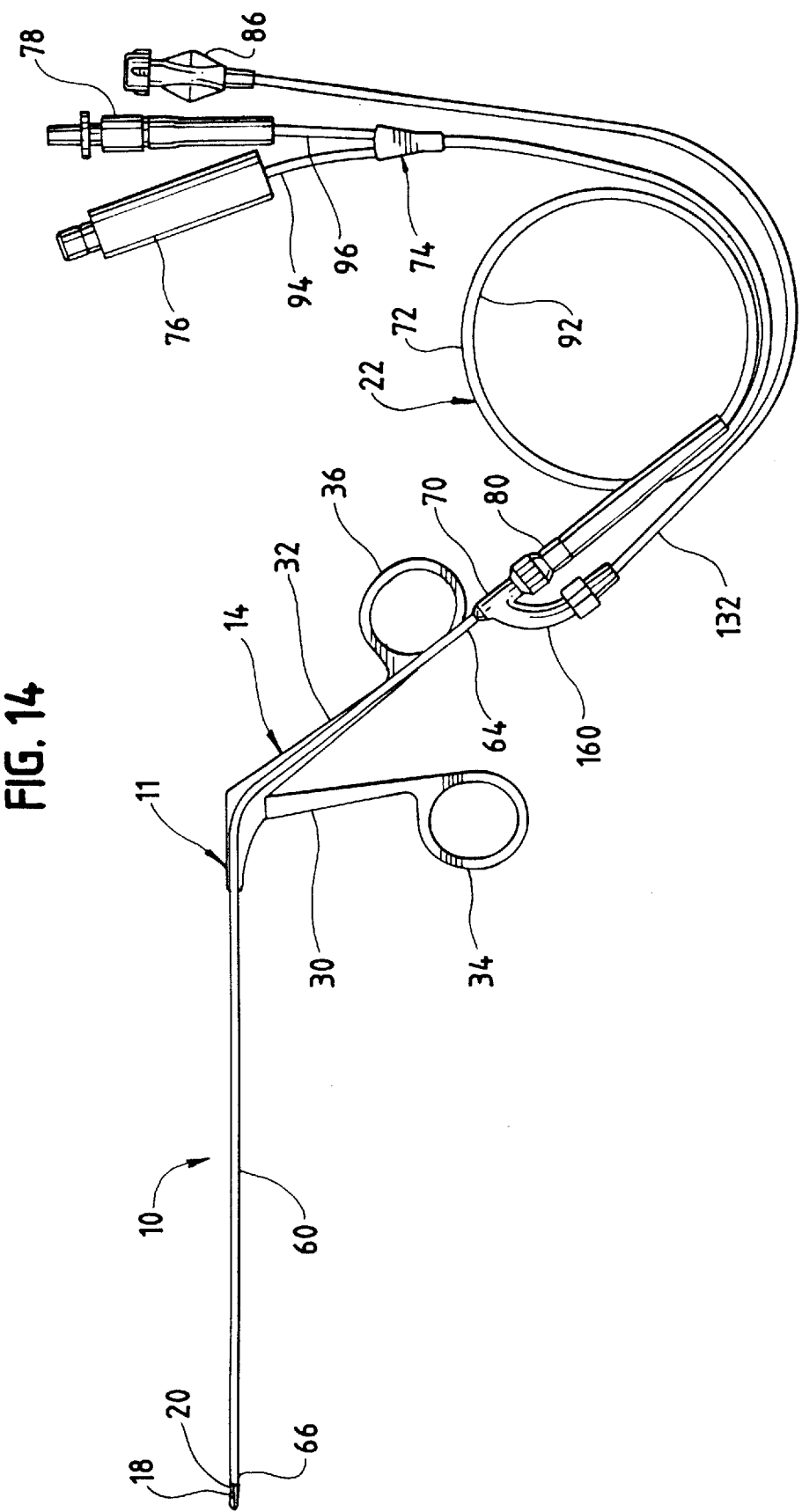
FIG. 14 is a side elevational view of the surgical instrument in accordance with a still further embodiment of the invention, illustrating an irrigation tube assembly joined to a mounting tube by a branch fitting.
Figure 15:
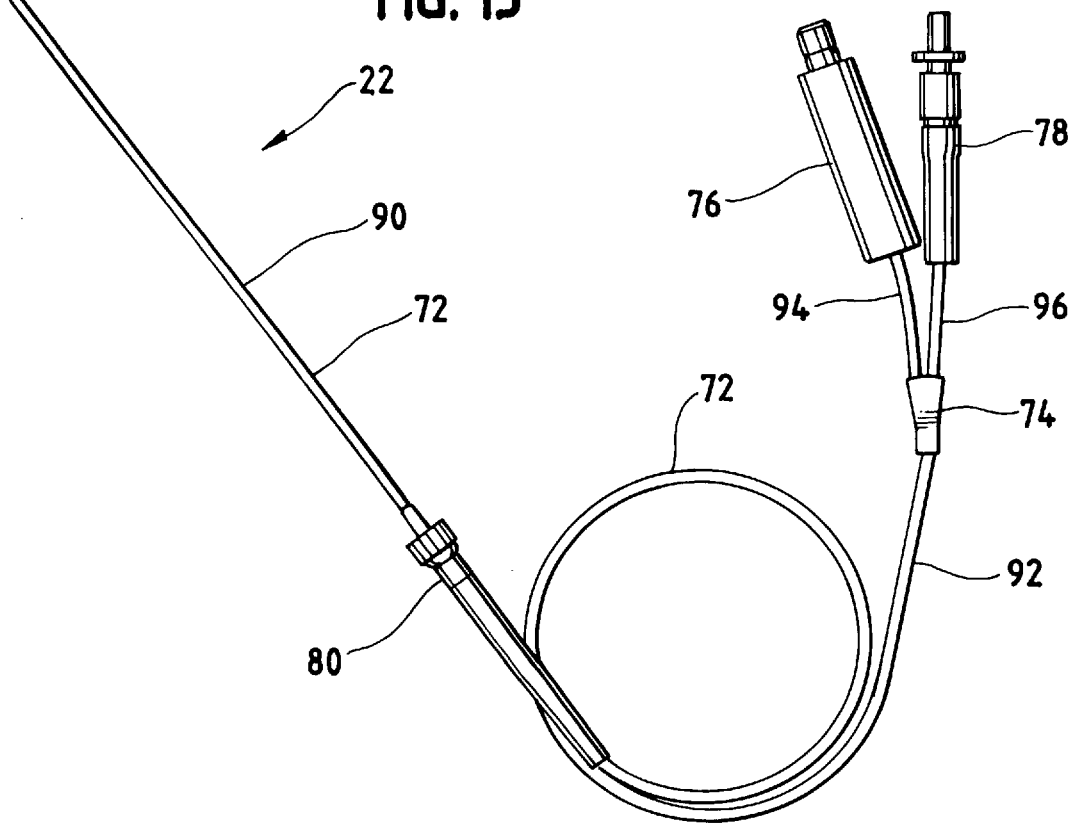
FIG. 15 is a side elevational view of an endoscope of the surgical instrument of FIG. 14 that does not include an irrigation channel.

As shown in FIG. 14, instead of the connector assembly described above, the first connector 70 may include a branch fitting 160 mounted on the distal end of the irrigation tube 132 that is attachable to the center connector 140. In the illustrated embodiment, the branch fitting 160 extends from the mounting tube 60 for attachment to the center connector 140. The endoscope 22 of FIG. 15, which does not include an irrigation channel, may be used with the surgical tool 11 of FIG. 14.

Alternatively, in accordance with the embodiment of FIG. 16, the endoscope 22 may define an irrigation channel 110 that extends substantially the entire length of the endoscope 22 for providing the irrigation fluid to the distal end of the endoscope. The irrigation channel 110 is encased by the sheath 72 and thus preferably is flexible. The irrigation channel 110 may be defined by an irrigation tube contained within the endoscope. The irrigation channel 110 passes through the hub member 82, to the irrigation tube segment 84, and to the irrigation tube connector 86 that is attachable to the irrigation fluid supply system for providing the irrigation fluid.

The endoscope 22 containing an irrigation channel that extends all or part of the length of the endoscope is generally intended to be disposable after a single use because the irrigation channel desirably has a relatively small diameter and thus is difficult to clean.

Figure 17:
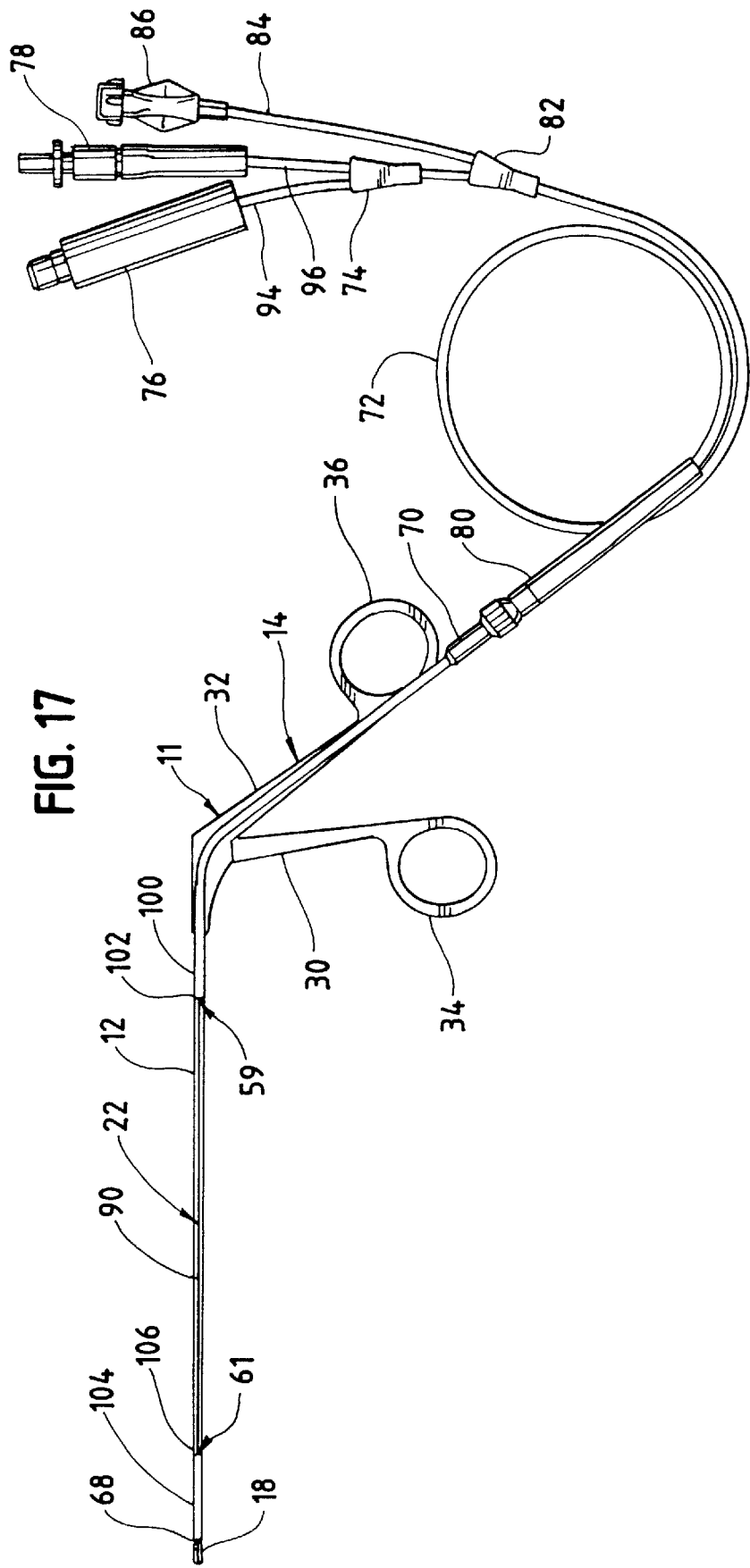
FIG. 17 is a side elevational view of a further embodiment of the surgical instrument, illustrating an alternative embodiment of a mount for mounting an endoscope to a shaft of the instrument in the form of a proximal mounting tube and a distal mounting tube.

Other mounts can be included for removably mounting the endoscope 22 to the shaft 12. In FIG. 17, for example, the instrument 10 includes a proximal mount 100 mounted to a proximal portion 102 of the shaft 12 and a distal mount 104 mounted to a distal portion 106 of the shaft 12. In the illustrated embodiment, the proximal mount 100 is also secured to the handle 14 and extends to the proximal end of the handle. The handle 14 may be offset relative to the proximal portion 102 of the shaft 12. If desired, the proximal and distal portions 102 and 106 may be offset relative to each other. Because the endoscope 22 is flexible, it can be readily secured to the shaft 12 and the handle 14 if the handle is offset relative to the shaft or if the proximal and distal portions of the shaft are offset.

In the embodiment of FIG. 17, the proximal and distal mounts 100 and 104 are in the form of proximal and distal mounting tubes that define respective longitudinal bores 59 and 61 for receiving respective portions of the distal portion 90 of the endoscope 22. The first connector 70 (which may be a luer or an SMA connector) may be secured to a proximal end of the proximal mount 100 for attachment to second connector 80 (which may be another luer or SMA connector) of the endoscope 22. A distal end of the distal mount 104 may define the bulbous atraumatic tip 68 to enhance the tactile response of the instrument 10. The proximal and distal mounts 100 and 104 may either be spaced or a continuous or unitary mount such as the tube 60 shown in FIGS. 1–3. Instead of mounting tubes, the proximal and distal mounts 100 and 104 may be in any other suitable form, such as, for example, a molded or shrinkable tubing adapted to form a secure compression fitting or shrinkable coupling, which is particularly useful for irregularly-shaped shafts. The tubing can be heat, water or chemically shrinkable.

In FIG. 18, a surgical tool 151 in accordance with another embodiment of the invention is illustrated in the form of a scissors tool. The tool 151 includes an elongated shaft 152 with a handle 154 mounted on a proximal end 156 of the shaft, and a working element in the form of a scissors 158 mounted on a distal end 159 of the shaft. A mounting tube 160 is mounted to the exterior of the shaft 152 and handle 154, extending along substantially the entire length of the shaft and the handle. The mounting tube 160 defines a longitudinal bore 162 extending between a proximal end 164 and a distal end 166 of the mounting tube for receiving a flexible endoscope. A first connector 170 (such as a luer or an SMA connector) is mounted on the proximal end 164 of the mounting tube 160, extending proximally of the handle 154, for attachment to second connector 80 (such as another luer or an SMA connector) mounted along the length of the endoscope as describe above. The tool is designed so that the scissors-action can be imparted to the scissors 158 by squeezing together a pair of buttons 174 mounted on opposite sides of the shaft, in accordance with surgical scissors instruments known in the art.

In FIG. 19, another alternative embodiment of the surgical instrument is illustrated that may be bendable or include a predetermined bend. The surgical instrument includes mounts 200 and 202 preferably on those portions of the shaft 12 that are not bent or do not flex. In the illustrated embodiments, a working element 218 in the form of a scissors is provided, and the mounts 200 and 202 are mounted respectively on the proximal and distal portions 102, 106 of the shaft 12. The mounts 200 and 202 may be tubes molded or shrunk to respective portions of the shaft 12 to retain the endoscope 22. If desired, however, a bonding agent can be used. Also, the mounts 200 and 202 and endoscope 22 can be flexible to allow the endoscope 22 to be adjusted with the shaft 12, without interrupting or misaligning the view.

Any suitable viewing system may be used in accordance with the invention. The viewing system may, for example, include an eyepiece (not shown), which provides direct viewing of the image focused upon the distal end of the image fiber bundle by the objective lens. However, the image may also be fed to a video camera whose output is transmitted to a viewing screen or monitor for observation by the surgeon and the surgical support staff.

Additionally, if desired, one or more illumination fibers 52 may be included as part of the same bundle as the image fiber bundle 50. If desired, the surgical instrument in accordance with the present invention can include more than one endoscope or optical assembly.

The optical assembly may, if desired, be a single image fiber bundle in the form of a rod lens, alone or in combination with a fiberoptic bundle. The rod lens may be mounted on the shaft 12 and operably coupled to a flexible fiberoptic bundle having a plurality of image fiber bundles to provide a beneficial configuration of a small optical system on the operating portion of the instrument while still having the benefits of a flexible fiberoptic bundle extending from the handle 14.

Figure 20:
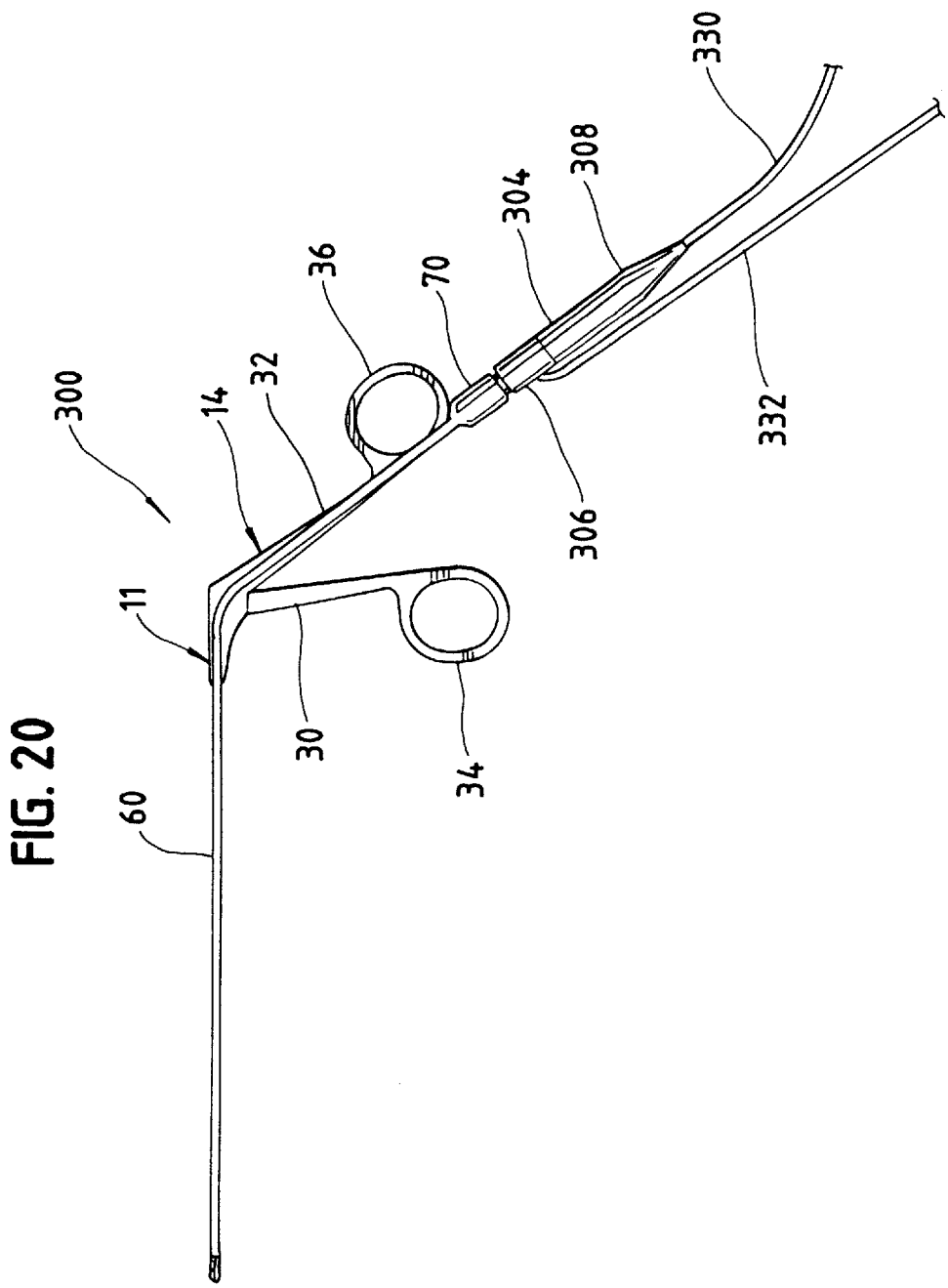
FIG. 20 is a side elevational view of the surgical instrument in accordance with a further embodiment of the invention, including an alternative embodiment of an endoscope and a CCD camera head assembly removably secured to the endoscope.

FIGS 20–22 illustrate a surgical instrument 300 in accordance with alternative embodiments of the invention, including an endoscope 302 that is secured to a CCD camera head assembly 304 by, for example, a second connector 306 mounted on the endoscope. The endoscope may be secured to the shaft by the second connector 306 and by the mounting tube 60 and the first connector 70 in accordance with the above-described embodiments.

The CCD camera head assembly 304 includes a casing 308, a CCD camera head 310, a CCD chip 312, and a focusing lens system 320 for focusing an image onto the CCD chip 312. The CCD camera head 310 preferably has an outer diameter of about ¼ inch (about 7 mm). In the embodiment of FIGS. 21 and 22, the focusing lens system 320 includes a focusing ring 322 and a lens 324, and a channel 326 is defined within the casing 308 to permit sliding of the lens 324 by the focusing ring 322 to bring the image into focus. An electric cord 330 extends from the CCD camera head assembly 304 to a television monitor. A tubing 332 extends from the second connector 306 that contains illumination fibers and, if desired, an irrigation tube.

A proximal end of the second connector 306 is removably secured to the CCD camera head assembly 304 preferably so that a distal end of an image fiber bundle 342 extending within the endoscope 302 is a predetermined distance from the CCD camera head 310 or the focusing lens 324 so that the image can readily be brought into focus. In the illustrated embodiment, a first mating portion 344 having a male thread 346 is defined at the proximal end of the second connector 306. A second mating portion 348 having a female thread is defined at a distal end of the casing 308 of the CCD camera head assembly 304. The first mating portion 344 is adapted to extend within the casing 308 and threadingly engage the second mating portion 348.

The embodiment of FIGS. 20–22 provides many advantages. For example, it enables the endoscope to be readily and easily secured adjacent the CCD camera head 310 so that the distal end of the image fiber bundle 342 and the focusing lens 324 or CCD camera head are spaced apart by a predetermined distance. Thus, the image can be readily and easily brought into focus. With this construction, the endoscope 302 can be disposable, with the camera head assembly 304 being reusable with other endoscopes. This is a significant advantage because CCD chips and camera heads tend to be relatively expensive components.

With the embodiments of FIGS. 20–22, the CCD camera head 310 is positioned at a location that does not interfere with the surgical procedure and does not significantly affect the control and tactile feel of the instrument. The CCD camera head is sufficiently close to the surgical site, yet positioned so that it should not come into contact with the surgical site. The camera head assembly 304 also preferably is compact and lightweight so that it does not add any significant bulk or weight to the surgical instrument. These embodiments also permit the CCD camera head to be heavily insulated by the casing 308 or other suitable insulation without interfering with the surgical procedure and without significantly affecting the control and tactile feel of the instrument.

The present invention also includes a method of retrofitting an existing surgical instrument with the endoscope 22. The method starts with an existing surgical tool 11 that includes the shaft 12 described above having proximal end 16 and distal end 20, the handle 14 connected to the proximal end of the shaft, and the working element 18 connected to the distal end of the shaft. The handle 14 includes a gripping portion and is offset relative to the shaft. The flexible endoscope 22 described above is provided. The mounting tube 60 described above is secured to the shaft 12 so that the mounting tube extends along substantially the entire length of the shaft 12 and along the gripping portion. The endoscope 22 is removably mounted to the shaft 12 by attaching the first and second connectors 70, 80 so that the distal portion 90 of the endoscope is received within the mounting tube 60 and extends along substantially the entire length of the shaft 12 and along the gripping portion and so that a distal end of the endoscope can be used to view the working element.

To help align the distal end of the endoscope 22 to provide a proper field of view, a reference gauge can be used. The reference gauge includes at least two steps, one for the end of the tool 11 and one for the distal end of the endoscope 22 while the endoscope is being mounted to the shaft 12.

Although the prior art has been described with reference to certain preferred embodiments, numerous modifications and variations can be made by those skilled in the art without departing from the novel spirit and scope of this invention.

What is claimed is:

1. A surgical instrument for use with a viewing system comprising:
    (a) an elongated shaft having a proximal portion and a distal portion;
    (b) a handle mounted on the proximal portion of the shaft and having a gripping portion adapted to be held by a user of the instrument, the handle being offset relative to the shaft;
    (c) a working element mounted on the distal portion of the shaft for manipulating tissue during the course of a surgical procedure;
    (d) an elongated endoscope including at least one image fiber bundle and having a distal end and a proximal end adapted to be operably coupled to the viewing system, the endoscope including a first connector positioned between the distal end and the proximal end;
    (e) a proximal mount including a proximal tube extending onto at least part of the gripping portion and a second connector attached to the proximal tube and adapted to removably receive the first connector for removably mounting the endoscope to the proximal portion of the shaft and to the handle; and
    (f) a distal mount for removably mounting the endoscope to the distal portion of the shaft so that the endoscope extends along the distal portion of the shaft.

2. The surgical instrument of claim 1 wherein the proximal mount is coupled to the exterior of the proximal portion of the shaft and the exterior of the handle and the distal mount is coupled to the exterior of the distal portion of the shaft.

3. The surgical instrument of claim 2 wherein the proximal tube extends along the proximal portion of the shaft and the distal mount includes a distal tube extending along the distal portion of the shaft.

4. The surgical instrument of claim 3 wherein the proximal and distal tubes are spaced apart from each other.

5. The surgical instrument of claim 3 wherein the proximal tube and the distal tube are unitary.

6. The surgical instrument of claim 3 wherein an atraumatic bulbous tip is provided on a distal end of the distal tube.

7. The surgical instrument of claim 3 wherein the proximal tube and the distal tube define portions of a unitary mounting tube that has a proximal end and a distal end and defines a longitudinal bore, the second connector being mounted to the proximal end of the mounting tube so that the distal portion of the endoscope extends within the longitudinal bore, and wherein the mounting tube and the endoscope define an irrigation passageway within the longitudinal bore for delivering an irrigation fluid to the distal end of the mounting tube, the irrigation passageway extending substantially the entire length of the mounting tube and adapted to be in fluid flow communication with an irrigation fluid supply system for supplying the irrigation fluid.

8. The surgical instrument of claim 1 wherein the endoscope defines an irrigation channel for providing an irrigation fluid to the distal end of the endoscope.

9. The surgical instrument of claim 1 further including an irrigation tube adapted to be removably mounted to the proximal mount for providing an irrigation fluid to the distal end of the endoscope, and adapted to be operably coupled to an irrigation fluid supply system for supplying the irrigation fluid to the irrigation tube.

10. The surgical instrument of claim 1 wherein the proximal mount extends along substantially the entire length of the handle.

11. The surgical instrument of claim 1 wherein the handle is offset relative to the shaft.

12. The surgical instrument of claim 1 wherein the shaft is flexible.

13. The surgical instrument of claim 1 wherein the distal portion of the shaft is displaceable to alternative positions wherein the distal portion of the shaft does not have the same axis as the proximal portion of the shaft.

14. The surgical instrument of claim 1 wherein the shaft is malleable.

15. The surgical instrument of claim 1 wherein the endoscope includes an illumination fiber.

16. The surgical instrument of claim 1 further including a CCD camera head assembly having a CCD camera head and being removably engageable with the proximal end of the endoscope.

17. The surgical instrument of claim 16 wherein the proximal end of the endoscope includes a first mating portion and the CCD camera head assembly further includes a casing having a distal end that includes a second mating portion, the mating portions engageable to removably secure the endoscope to the CCD camera head assembly.

18. The surgical instrument of claim 17 wherein the first and second mating portions are threadingly engageable, the second mating portion defined on an inner wall of the casing so that the first mating portion is adapted to be received within the casing.

19. The surgical instrument of claim 16 wherein the CCD camera head assembly includes a CCD chip and a focusing lens that is movable relative to the CCD chip.

20. A surgical instrument for use with a viewing system, including:
(a) an elongated shaft having a proximal end and a distal end;
(b) a handle mounted on the proximal end of the shaft and having a gripping portion adapted to be held by a user of the instrument, the handle being offset relative to the shaft;
(c) a working element mounted on the distal end of the shaft for manipulating tissue during a surgical procedure;
(d) an elongated flexible endoscope having a proximal end, a distal end and a first connector positioned between the proximal and distal ends of the endoscope to define a proximal portion and a distal portion of the endoscope, the endoscope having at least one image fiber bundle with a proximal end adapted to be operably coupled to the viewing system; and
(e) a mounting tube extending along the shaft and onto the gripping portion of the handle, the mounting tube defining a bore for removably mounting the endoscope to the shaft and handle of the tube and including a second connector, the first and second connectors being attachable to removably secure the endoscope to the mounting tube.

21. The surgical instrument of claim 20 wherein the mounting tube extends along substantially the entire length of the shaft and along substantially the entire length of the handle.

22. The surgical instrument of claim 20 wherein the endoscope defines an irrigation channel for delivering an irrigation fluid to the distal end of the endoscope.

23. The surgical instrument of claim 20 wherein the mounting tube includes a proximal end and a distal end and the bore extends between the proximal and distal ends of the mounting tube, the second connector being mounted to the proximal end of the mounting tube so that the distal portion of the endoscope extends within the bore, and wherein the mounting tube and the endoscope define an irrigation passageway within the bore for delivering an irrigation fluid to the distal end of the mounting tube, the irrigation passageway extending substantially the entire length of the mounting tube and adapted to be in fluid flow communication with an irrigation fluid supply system for supplying the irrigation fluid.

24. The surgical instrument of claim 23 wherein the proximal portion of the endoscope defines an irrigation channel for providing fluid flow communication between the irrigation passageway and the irrigation fluid supply system.

25. The surgical instrument of claim 23 further including an irrigation tube adapted to be joined to the mounting tube for providing fluid flow communication between the irrigation passageway and the irrigation fluid supply system.

26. The surgical instrument of claim 25 wherein the second connector includes a fitting for joining together the mounting tube and the irrigation tube to provide fluid flow communication between the irrigation tube and the irrigation passageway.

27. The surgical instrument of claim 26 wherein the fitting includes a branch fitting attachable to a distal end of the irrigation tube.

28. The surgical instrument of claim 27 wherein the branch fitting is attachable to the distal end of the irrigation tube by a third connector mounted to the distal end of the irrigation tube.

29. The surgical instrument of claim 23 wherein at least one aperture is defined on the mounting tube for reducing the fluid pressure of the irrigation fluid at the distal end of the mounting tube.

30. The surgical instrument of claim 20 wherein an atraumatic bulbous tip is provided on a distal end of the mounting tube.

31. The surgical instrument of claim 20 wherein the shaft and mounting tube are malleable by a user of the instrument.

32. The surgical instrument of claim 20 wherein the mounting tube has a predetermined curve.

33. A surgical instrument for use with a viewing system, including:
(a) an elongated shaft having a proximal end and a distal end;
(b) a handle mounted on the proximal end of the shaft and adapted to be held by a user of the instrument;
(c) a working element mounted on the distal end of the shaft for manipulating tissue during a surgical procedure;
(d) a mounting tube secured to the shaft and handle and extending along substantially the entire length of the shaft and along substantially the entire length of the handle, the mounting tube having a distal end and a proximal end and defining a longitudinal bore extending between the proximal and distal ends of the mounting tube;
(e) a flexible optical assembly, the optical assembly having a proximal end and a distal end and including at least one image fiber bundle having a proximal end adapted to be operably coupled to the viewing system, the optical assembly adapted to extend within the longitudinal bore and be removably mounted to the shaft by the mounting tube;
(f) an irrigation tube for providing an irrigation fluid to the distal end of the mounting tube, the irrigation tube adapted to be in fluid flow communication with an irrigation fluid supply system; and
(g) a connector assembly for removably securing the irrigation tube to the mounting tube for providing fluid flow communication between the longitudinal bore and the irrigation tube, and for removably securing the irrigation tube to the optical assembly so that the optical assembly extends along substantially the entire length of the shaft and along substantially the entire length of the handle.

34. The surgical instrument of claim 33 wherein the connector assembly includes a first connector mounted to a distal end of the irrigation tube, the first connector includes a proximal end and a distal end and defines a channel to provide fluid flow communication between the longitudinal bore of the mounting tube and the irrigation tube.

35. The surgical instrument of claim 34 wherein the channel extends between the proximal and distal ends of the first connector, the channel adapted to receive a portion of the optical assembly so that the first connector is slidingly engageable with the optical assembly.

36. The surgical instrument of claim 34 wherein the first connector is mounted to the distal end of the irrigation tube between the proximal and distal ends of the first connector.

37. The surgical instrument of claim 35 wherein the proximal end of the first connector is attachable to the distal end of the mounting tube to removably secure the irrigation tube to the mounting tube.

38. The surgical instrument of claim 37 wherein the connector assembly further includes a distal connector mounted to the proximal end of the mounting tube, the first connector being attachable to the distal connector.

39. The surgical instrument of claim 38 wherein the first and distal connectors are luers matingly engageable with each other.

40. The surgical instrument of claim 34 wherein the connector assembly further includes a proximal connector mounted to the optical assembly proximal of the distal end of the optical assembly, the proximal end of the first connector attachable with the proximal connector to removably secure the optical assembly to the irrigation tube.

41. The surgical instrument of claim 40 wherein the first and proximal connectors are luers matingly engageable with each other.

42. The surgical instrument of claim 40 wherein the channel extends between the proximal and distal ends of the first connector and is adapted to receive a distal portion of the optical assembly, the first connector adapted to be slidingly engageable with the distal portion of the optical assembly.

43. The surgical instrument of claim 33 wherein an atraumatic bulbous tip is provided on the distal end of the mounting tube.

44. The surgical instrument of claim 33 wherein the handle is offset relative to the shaft.

45. The surgical instrument of claim 43 wherein the shaft and the mounting tube are malleable by the user.

46. The surgical instrument of claim 43 wherein the mounting tube has a predetermined curve.

47. The surgical instrument of claim 43 wherein the optical assembly includes an illumination fiber.

48. A method of retro-fitting a surgical tool with a flexible endoscope having at least one image fiber bundle, a proximal end, a distal end, and a first connector between the proximal and distal ends of the endoscope to define a distal portion of the endoscope, the method comprising the steps of:
(a) providing the surgical tool to be retro-fit, the tool including a shaft having a proximal end and a distal end, a working element on the distal end of the shaft, and a handle on the proximal end of the shaft having a gripping portion and being offset relative to the shaft;
(b) securing to the shaft and handle a mounting tube having a proximal end and a second connector positioned at the proximal end of the mounting tube, such that the mounting tube extends along substantially the entire length of the shaft and along the gripping portion; and
(c) removably mounting the endoscope to the shaft by attaching together the first and second connectors such that the distal portion of the endoscope is received within the mounting tube and extends along substantially the entire length of the shaft and along the gripping portion and such that a distal end of the endoscope is positioned near the working element.

49. The method of claim 48 wherein the mounting tube has a predetermined bend.

50. The method of claim 48 wherein the securing step includes applying a solder to attach the mounting tube to the shaft and handle.

51. The method of claim 48 wherein the mounting step includes using a reference gauge to align a distal end of the endoscope with the working element.

52. The method of claim 48 wherein the mounting tube defines a longitudinal bore extending substantially the entire length of the mounting tube for receiving the distal portion of the endoscope, and wherein the mounting tube and the distal portion of the endoscope define an irrigation passageway within the longitudinal bore for providing an irrigation fluid to a distal end of the mounting tube, the irrigation passageway adapted to be in fluid flow communication with an irrigation fluid supply system for providing the irrigation fluid.

53. The method of claim 52 further including a step of mounting an irrigation tube to the mounting tube, the irrigation tube adapted to provide fluid flow communication between the irrigation passageway and the irrigation fluid supply system.

54. The method of claim 48 wherein the endoscope defines an irrigation channel for providing an irrigation fluid to a distal end of the mounting tube, the irrigation channel adapted to be in fluid flow communication with an irrigation fluid supply system for providing the irrigation fluid.

55. An endoscope for use with a surgical tool having a shaft that includes proximal and distal ends, a handle that includes a gripping portion offset from the shaft, a working element mounted on the distal end of the shaft, a mounting tube externally mounted to the shaft and gripping portion that includes a proximal end and defines a longitudinal bore of a predetermined length, and a first connector mounted on the proximal end of the mounting tube, the endoscope comprising:
(a) a proximal end adapted to be operably coupled to a viewing system;
(b) a distal end;
(c) an image fiber bundle having a distal end with an objective lens mounted thereon; and
(d) a second connector mounted on the endoscope proximally of the distal end of the endoscope to define proximal and distal portions, the distal portion being flexible, having a length substantially equal to the length of the longitudinal bore and adapted for sliding within the longitudinal bore of the mounting tube, the second connector adapted for attaching to the first connector to removably secure the endoscope to the mounting tube with the objective lens positioned for defining a field of view which includes at least part of the working element, wherein the proximal portion of the endoscope defines an irrigation channel terminating adjacent a distal end of the second connector.

56. The endoscope of claim 55 further including an illumination fiber.

57. A flexible endoscope for use with a surgical tool having a shaft that includes proximal and distal ends, a handle mounted on the proximal end of the shaft that includes a gripping portion offset relative to the shaft, a working element mounted on the distal end of the shaft, and a bent mounting tube externally mounted to the shaft and gripping portion that includes proximal and distal ends and defines a bore, the mounting tube engageable with an irrigation tube by a first connector mounted on the irrigation tube for providing an irrigation fluid to the distal end of the mounting tube, the endoscope comprising:
(a) a proximal end adapted for coupling to a viewing system;
(b) a distal end;
(c) an image fiber bundle having a distal end with an objective lens mounted thereon; and
(d) a second connector mounted on the endoscope proximally of the distal end of the endoscope to define proximal and distal portions, the distal portion being flexible and adapted for sliding within the bore of the mounting tube, the second connector adapted for attaching to the first connector to removably secure the endoscope to the mounting tube with the distal end of the endoscope being substantially co-terminus with the distal end of the mounting tube and with the objective lens positioned for defining a field of view which includes at least part of the working element, wherein the proximal portion of the endoscope defines an irrigation channel terminating adjacent a distal end of the second connector.

58. The endoscope of claim 57 further including an illumination fiber.

59. A surgical tool for use with an endoscope having a distal end and a flexible distal portion and a connector, the tool comprising:

(a) an elongated shaft having a proximal end and a distal end;

(b) a handle mounted on the proximal end of the shaft and having a gripping portion offset with respect to the shaft;

(c) a working element on the distal end of the shaft;

(d) a mounting tube having a distal end proximate to the working element and a proximal end and a curve between the ends, the tube being secured along the length of the shaft and a substantial length of the gripping portion of the handle; and (e) a connector on the proximal end of the tube such that the distal portion of the endoscope can be received in the tube with the connector engaged with the endoscope connector and the distal end of the endoscope being positioned to view a surgical site during a surgical procedure.

* * * * *